United States Patent
Tegels et al.

(10) Patent No.: US 11,364,119 B2
(45) Date of Patent: Jun. 21, 2022

(54) RETRIEVAL AND REPOSITIONING SYSTEM FOR PROSTHETIC HEART VALVE

(71) Applicant: Tendyne Holdings, Inc., St. Paul, MN (US)

(72) Inventors: Zachary Tegels, Minneapolis, MN (US); Robert Vidlund, Forest Lake, MN (US); Mark Christianson, Plymouth, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 139 days.

(21) Appl. No.: 16/560,094

(22) Filed: Sep. 4, 2019

(65) Prior Publication Data

US 2020/0008942 A1 Jan. 9, 2020

Related U.S. Application Data

(60) Division of application No. 14/329,215, filed on Jul. 11, 2014, now Pat. No. 10,478,293, which is a continuation-in-part of application No. 14/154,816, filed on Jan. 14, 2014, now abandoned.

(60) Provisional application No. 61/808,458, filed on Apr. 4, 2013.

(51) Int. Cl.
*A61F 2/24* (2006.01)
*A61F 2/95* (2013.01)

(52) U.S. Cl.
CPC .......... *A61F 2/2427* (2013.01); *A61F 2/2418* (2013.01); *A61F 2/2439* (2013.01); *A61F 2/2472* (2013.01); *A61F 2/2457* (2013.01); *A61F 2/9517* (2020.05); *A61F 2250/0098* (2013.01)

(58) Field of Classification Search
CPC .... A61F 2/2427; A61F 2/2472; A61F 2/2418; A61F 2/2439; A61F 2/9517; A61F 2250/0098; A61F 2/2457
See application file for complete search history.

(56) References Cited

U.S. PATENT DOCUMENTS

| | | |
|---|---|---|
| 2,697,008 A | 12/1954 | Ross |
| 3,409,013 A | 11/1968 | Berry |
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |

(Continued)

FOREIGN PATENT DOCUMENTS

| | | |
|---|---|---|
| CN | 1486161 A | 3/2004 |
| CN | 1961845 A | 5/2007 |

(Continued)

OTHER PUBLICATIONS

US 9,155,620 B2, 10/2015, Gross et al. (withdrawn)

(Continued)

*Primary Examiner* — Jerrah Edwards
*Assistant Examiner* — Mihret Tafesse
(74) *Attorney, Agent, or Firm* — Wei & Sleman LLP

(57) ABSTRACT

This invention relates to the design and function of a retrieval device for a prosthetic heart valve for re-positioning or removal of a previously implanted valve prosthesis from a beating heart without extracorporeal circulation using a transcatheter retrieval system.

14 Claims, 13 Drawing Sheets

(56) References Cited

U.S. PATENT DOCUMENTS

| | | |
|---|---|---|
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A * | 9/1999 | Leonhardt ............ A61F 2/2436 623/1.24 |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |

(56) References Cited

U.S. PATENT DOCUMENTS

| | | |
|---|---|---|
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Altieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |

(56) References Cited

U.S. PATENT DOCUMENTS

| | | |
|---|---|---|
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |

(56) References Cited

U.S. PATENT DOCUMENTS

| | | |
|---|---|---|
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0271172 A1 | 11/2006 | Tehrani |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0255394 A1 | 11/2007 | Ryan |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0039934 A1 | 2/2008 | Styrc |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054969 A1* | 2/2009 | Salahieh ............... A61F 2/2436 623/1.26 |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1* | 11/2010 | Alkhatib ............... A61F 2/2418 623/2.11 |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |

(56) References Cited

U.S. PATENT DOCUMENTS

| | | |
|---|---|---|
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0208297 A1 | 8/2011 | Tuval et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016464 A1 | 1/2012 | Seguin |
| 2012/0016468 A1 | 1/2012 | Robin et al. |
| 2012/0022633 A1 | 1/2012 | Olson et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059458 A1 | 3/2012 | Buchbinder et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Mdlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0265401 A1 | 9/2015 | Braido |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0038280 A1 | 2/2016 | Morriss et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |

(56) References Cited

U.S. PATENT DOCUMENTS

| | | | |
|---|---|---|---|
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0263618 A1 | 9/2018 | Vidlund et al. |
| 2018/0271653 A1 | 9/2018 | Vidlund et al. |

FOREIGN PATENT DOCUMENTS

| | | | |
|---|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102869317 A | 1/2013 |
| CN | 102869318 A | 1/2013 |
| CN | 102869321 A | 1/2013 |
| CN | 103220993 A | 7/2013 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2013512765 A | 4/2013 |
| JP | 2013539395 A | 10/2013 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 200149213 A3 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 0176510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 03047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013021374 A2 | 2/2013 |
| WO | 2013021375 A2 | 2/2013 |
| WO | 2013045262 A1 | 4/2013 |
| WO | 2013059747 A1 | 4/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

European Search Report for Appln No. EP19211967, dated Mar. 27, 2020, 3 pages.

Office Action for U.S. Appl. No. 14/154,816, dated Dec. 22, 2015, 8 pages.

(56) References Cited

OTHER PUBLICATIONS

Al Zaibag, Muayed, et al., "Percutaneous Balloon Valvotomy in Tricuspid Stenos's," British Heart Journal, Jan. 1987, vol. 57, No. 1, pp. 51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Benchimol, A. et al., "Simultaneous Left Ventricular Echocardiography and Aortic Blood Velocity During Rapid Right Ventricular Pacing in Man," The American Journal of the Medical Sciences, Jan -Feb. 1977, 273(1):55-62.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration In Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

Gray, H., The Aorta, Anatomy of the Human Body, 1918, Retrieved from the Internet <http://www.bartleby.com/107/142.html>, Oct. 12, 2012, 5 pages.

Gray, H., The Heart, Anatomy of the Human Body, 1918, Retrieved from the Internet <http://education.yahoo.com/reference/gray/subjects/subject/138>, Oct. 10, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.

L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal of Artificial Organs, 1993, Issue 5, vol. 16, pp. 253-262.

Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, Georg, et al., Mitral valved stent implantation, European Journal of Cardio-Thoracic Surgery, 2010, vol. 38, pp. 350-355.

Ma, L. et al., "Double-crowned valved stents for off-pump mitral valve replacement," European Journal of Cardio-Thoracic Surgery, Aug. 2005, 28(2): 194-198.

Moazami, N. et al., "Transluminal aortic valve placement: A feasibility study with a newly designed collapsible aortic valve," ASAIO Journal, Sep./ Oct. 1996, 42(5):M381-M385.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966,196( 11 ): 173-174.

Rashkind, W. J., "Historical Aspects of Interventional Cardiology: Past, Present, Future," Texas Heart Institute Journal, Dec. 1986, 13(4):363-367.

Reul, H. et al., "The Geomety of the Aortic Root in Health, at Valve Disease and After Valve Replacement," J. Biomechanics, 1990, 23(2):181-191.

Rosch, J. et al., "The Birth, Early Years and Future of Interventional Radiology," J Vasc Interv Radiol., Jul. 2003, 4:841-853.

Ross, D. N., "Aortic Valve Surgery," Guys Hospital, London, 1968, pp. 192-197.

Rousseau, E. P. M. et al., "A Mechanical Analysis of the Closed Hancock Heart Valve Prosthesis," Journal of Biomechanics, 1998, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, Barry T., et al., "Modifications of Gianturco Expandable Wire Stents," AJR:150, May 1988, Dec. 3, 1987, pp. 1185-1187.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.

Webb, J. G. et al., "Percutaneous Aortic Valve Implantation Retrograde from the Femoral Artery," Circulation, 2006, 113:842-850.

Wheatley, M.D., David J., "Valve Prostheses," Rob & Smith's Operative Surgery, Fourth Edition, pp. 415-424, ButtenNorths 1986.

Yoganathan, A. P. et al., "The Current Status of Prosthetic Heart Valves," In Polymetric Materials and Artificial Organs, Mar. 20, 1983, pp. 111-150, American Chemical Society.

Andersen, H. R. et al., "Transluminal implantation of arlificial heart valves. Description of a new expandable aortic valve and initial results with implantation by catheter technique in closed chest pigs," European Heart Journal, 1992, 13(5):704-708.

Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.

Bernacca, G. M. et al., "Polyurethane heart valves: Fatigue failure, calcification, and polyurethane structure," Journal of Biomedical Materials Research, Mar. 5, 1997, 34(3):371-379.

"Shape Memory Alloys," Retrieved from the Internet: <http://webdocs.cs.ualberta.ca/~database/MEMS/sma.html>, Feb. 5, 2016, 3 pages.

(56) References Cited

OTHER PUBLICATIONS

International Search Report and Written Opinion for International Application No. PCT/IB2014/060821, dated Oct. 10, 2014, 10 pages.
Office Action for U.S. Appl. No. 14/219,591, dated Mar. 11, 2016, 18 pages.
Orton, C., "Mitralseal: Hybrid Transcatheter Mitral Valve Replacement," Symposium: Small Animal Proceedings, 2011, pp. 311-312.

* cited by examiner

RETRIEVAL AND REPOSITIONING SYSTEM FOR PROSTHETIC HEART VALVE

CROSS-REFERENCE TO RELATED APPLICATIONS

This application is a divisional of U.S. patent application Ser. No. 14/329,215, filed Jul. 11, 2014, which is a continuation-in-part of U.S. patent application Ser. No. 14/154,816, filed Jan. 14, 2014, which claims priority to and the benefit of U.S. Provisional Application No. 61/808,458, filed Apr. 4, 2013, the contents of each of which are incorporated by reference herein in their entirety.

BACKGROUND

Field of the Invention

This invention relates to a novel device and method for retrieval of a transcatheter heart valve replacement or for capture and repositioning of a deployed transcatheter heart valve replacement.

Background of the Invention

Valvular heart disease and specifically aortic and mitral valve disease is a significant health issue in the US. Annually approximately 90,000 valve replacements are conducted in the US. Traditional valve replacement surgery, the orthotopic replacement of a heart valve, is an "open heart" surgical procedure. Briefly, the procedure necessitates a surgical opening of the thorax, initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients.

Thus if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated to the native mitral valve apparatus and thus a greater level of difficulty with regards to inserting and anchoring the replacement prosthesis.

Several designs for catheter-deployed (transcatheter) aortic valve replacement are under various stages of development. The Edwards SAPIEN® transcatheter heart valve is currently undergoing clinical trial in patients with calcific aortic valve disease who are considered high-risk for conventional open-heart valve surgery. This valve is deployable via a retrograde transarterial (transfemoral) approach or an antegrade transapical (transventricular) approach. A key aspect of the Edwards SAPIEN® and other transcatheter aortic valve replacement designs is their dependence on lateral fixation (e.g. tines) that engages the valve tissues as the primary anchoring mechanism. Such a design basically relies on circumferential friction around the valve housing or stent to prevent dislodgement during the cardiac cycle. This anchoring mechanism is facilitated by, and may somewhat depend on, a calcified aortic valve annulus. This design also requires that the valve housing or stent have a certain degree of rigidity.

At least one transcatheter mitral valve design is currently in development. The Endovalve uses a folding tripod-like design that delivers a tri-leaflet bioprosthetic valve. It is designed to be deployed from a minimally invasive transatrial approach, and could eventually be adapted to a transvenous atrial septotomy delivery. This design uses "proprietary gripping features" designed to engage the valve annulus and leaflets tissues. Thus the anchoring mechanism of this device is essentially equivalent to that used by transcatheter aortic valve replacement designs.

Various problems continue to exist in this field, including problems with how to retrieve a collapsible heart valve prosthetic from the native valve once the prosthetic has reached the end of its useful life. For example, a prosthetic heart valve may be delivered and secured percutaneously or intravenously using a catheter and endoscope or similar device, but the process of disengaging anchoring mechanisms and collapsing the prosthetic for retrieval is often more difficult to accomplish than is the delivery. Accordingly, there is a need for an improved device and method for retrieval when such valves need to be replaced.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In one embodiment, there is provided a prosthetic heart valve retrieval and repositioning device, comprising: a dilator sheath, said dilator sheath having a lumen therethrough and a dilator base mounted on a proximal side of said dilator sheath, said dilator base having a sheath lock for operatively engaging the dilator sheath for opening and closing the lumen of said dilator sheath, said dilator base having a slidably removable inner catheter disposed within the lumen, said inner catheter having a tapered tip at a distal end and an inner catheter base at a proximal end wherein said inner catheter base is adjacent and proximal to the dilator base, said dilator base having a guide rod aperture for engaging a guide rod that is connected to a guide rod handle mount that is attached to a handle apparatus, said inner catheter base having a traveler strap affixed on a proximal side and said traveler strap extending proximally to engage a tensioning unit on the handle apparatus, said handle apparatus having an actuator and a spring operatively connected to the traveler strap, wherein when the actuator is engaged the traveler strap is pulled proximally through the tensioning unit and the inner catheter base slides along guide rod towards the handle apparatus.

In another preferred embodiment, there is provided a prosthetic heart valve retrieval and removal device, comprising: a dilator sheath having a lumen therethrough and a dilator base mounted on a proximal side of said dilator sheath, said dilator base having a sheath lock for operatively engaging the dilator sheath for opening and closing the lumen of said dilator sheath, said dilator base having a slidably removable intermediate beveled catheter disposed within the lumen, said intermediate beveled catheter having an intermediate base mounted on a proximal side of said intermediate beveled catheter, said intermediate beveled catheter having a lumen therethrough and having inner catheter having a tapered tip at a distal end disposed within the intermediate beveled catheter, said inner catheter having an inner catheter base mounted on a proximal side of said inner catheter, wherein said inner catheter base is adjacent and proximal to the intermediate base and said intermediate base is adjacent and proximal to the dilator base, said dilator base having a guide rod aperture for engaging a guide rod that is connected to a guide rod handle mount that is attached to a handle apparatus, said inner catheter base having a traveler strap affixed on a proximal side and said traveler strap extending proximally to engage a tensioning unit on the handle apparatus, said handle apparatus having an actuator and a spring, wherein when the actuator is engaged the traveler strap is pulled proximally through the tensioning unit and the inner catheter base slides along guide rod towards the handle apparatus.

In another preferred embodiment, there is provided a prosthetic heart valve retrieval device wherein the tapered tip is bullet-shaped, cone-shaped, hooded, or otherwise shaped to guide the valve tether into the lumen of the dilator sheath.

In another preferred embodiment, there is provided wherein the dilator has a radio band affixed thereto.

In another preferred embodiment, there is provided a method of using the retrieval device for capturing a tethered expandable prosthetic heart valve to retrieve and re-position said valve, comprising the steps of: (i) inserting said retrieval and repositioning device into a body cavity of a patient containing a tethered and expandable prosthetic heart valve into a patient, (ii) capturing and retracting the tether into the retrieval device, and (iii) repositioning the tethered expandable prosthetic heart valve.

In another preferred embodiment, the method of retrieving and re-positioning also includes the step of (iv) removing the tethered and expandable heart valve from the patient by collapsing the expandable prosthetic heart valve apparatus into the dilator sheath catheter and retracting the dilator sheath.

In another preferred embodiment, there is provided a method of using the retrieval device for capturing a tethered expandable prosthetic heart valve to retrieve and remove said valve, comprising the steps of: (i) inserting said retrieval and removal device into a body cavity of a patient containing a tethered and expandable prosthetic heart valve into a patient, and (ii) capturing and retracting the tethered expandable prosthetic heart valve into the retrieval and removal device.

In another preferred embodiment, there is provided wherein the step of inserting the retrieval device by directly accessing the heart through the intercostal space, or using an apical approach to enter a heart ventricle.

In another preferred embodiment, there is provided wherein the step of inserting the retrieval device by directly accessing the heart through a thoracotomy, sternotomy, or minimally-invasive thoracic, thoroscopic, or trans-diaphragmatic approach to enter the left ventricle.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The attached figures provide enabling and non-limiting example of certain features of the present invention. The figures are not intended to be limiting in any way to the description that is provided in the text.

FIG. 13 shows the tapered tip of the inner catheter engaging the strut bundle of the valve and expelling the deployed valve from the annulus into an atrial location of the demonstration model.

FIG. 14 shows the tapered tip of the inner catheter engaging the strut bundle of the valve and expelling the deployed valve from the annulus into an atrium location of the demonstration model.

FIG. 23 shows the tapered tip of the inner catheter engaging the strut bundle of the valve just prior to expelling the deployed valve from the annulus into an atrial location of the demonstration model.

FIG. 25 also shows the catheter extending across the lumen of the ventricle of the model with the gated-bore collar outside of the body wall access port (proximal side) and the valve being removed from inside an atrial space of the demonstration model.

FIG. 26 also shows radio-marker band at the tip of the outer catheter.

DETAILED DESCRIPTION

Figure 1:
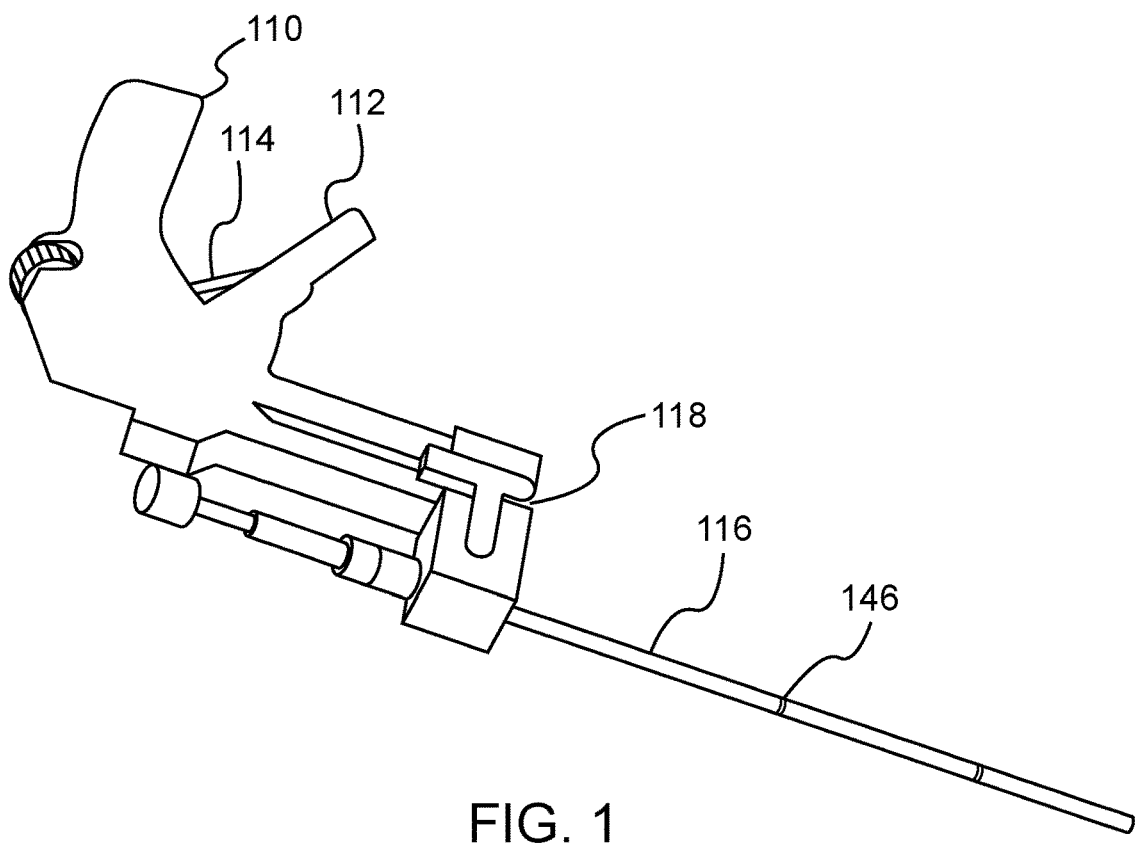
FIG. 1 is a side perspective view of one embodiment of a handle and support/pusher rod apparatus for the prosthetic valve retrieval system provided herein.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

Functions of the Retrieval System

The present invention provides in one embodiment a retrieval system for a previously deployed prosthetic heart valve wherein a valve tether is attached to the valve or to a collapsible stent containing the valve and the apparatus provided herein provides a method for capturing the tether of said valve, dislodging the deployed valve from the valve annulus, and then either re-positioning the valve and redeploying it, or removing the valve entirely.

The invention also allows for the capture of one or more retrieval tethers by a catheter-based extraction device, and for the re-positioning or removing the entire deployed valve apparatus via the retrieval device using an outpatient catheterization procedure without requiring major surgery.

Access & Deployment of the Retrieval Device

In one aspect of the retrieval, the catheter retrieval system accesses the heart and pericardial space by intercostal delivery. In this case, the pusher unit and catheters may be short, e.g. 12-38 cm.

In another retrieval approach, the catheter retrieval system retrieves the prosthetic heart valve using either an antegrade or retrograde approach using a flexible catheter system, and without requiring the rigid tube system commonly used. In another embodiment, the catheter system accesses the heart via a trans-septal approach. In either case, where a long distance must be traveled the pusher unit and associated catheters and equipment is contemplated as being within the range of 60-150 cm long.

Prosthetic Valve Devices

The prosthetic heart valve contemplated for retrieval using the retrieval device comprises a self-expanding tubular stent having a cuff at one end and tether loops for attaching tether(s) at the other end, and disposed within the tubular stent is a leaflet assembly that contains the valve leaflets, the valve leaflets being formed from stabilized tissue or other suitable biological or synthetic material. In one embodiment, the leaflet assembly comprises a wire form where a formed wire structure is used in conjunction with stabilized tissue to create a leaflet support structure which can have anywhere from 1, 2, 3 or 4 leaflets, or valve cusps disposed therein. In another embodiment, the leaflet assembly is wireless and uses only the stabilized tissue and stent body to provide the leaflet support structure, without using wire, and which can also have anywhere from 1, 2, 3 or 4 leaflets, or valve cusps disposed therein.

The tether anchors the valve to an anchoring location within the ventricle. Preferably, the location is the apex of the heart and uses an epicardial attachment pad. However, other tether attachment locations may be used in the deployment of the valve and also therefore, for the retrieval.

The cuff of the valve functions to counter the forces that act to displace the prosthesis toward/into the ventricle (i.e., atrial pressure and flow-generated shear stress) during ventricular filling. Accordingly, the stent containing the valve is positioned and pulled between the ventricular tether and the atrial cuff.

Cuff Structure

The cuff is a substantially flat plate that projects beyond the diameter of the tubular stent to form a rim or border. As used herein, the term cuff, flange, collar, bonnet, apron, or skirting are considered to be functionally equivalent. When the tubular stent is pulled through the mitral valve aperture, the mitral annulus, by the tether loops in the direction of the left ventricle, the cuff acts as a collar to stop the tubular stent from traveling any further through the mitral valve aperture. The entire prosthetic valve is held by longitudinal forces between the cuff which is seated in the left atrium and mitral annulus, and the ventricular tethers attached to the left ventricle.

The cuff is formed from a stiff, flexible shape-memory material such as the nickel-titanium alloy material Nitinol® wire that is covered by stabilized tissue or other suitable biocompatible or synthetic material. In one embodiment, the cuff wire form is constructed from independent loops of wire that create lobes or segments extending axially around the circumference of the bend or seam where the cuff transitions to the tubular stent (in an integral cuff) or where the cuff is attached to the stent (where they are separate, but joined components).

Once covered by stabilized tissue or material, the loops provide the cuff with the ability to travel up and down, to articulate, along the longitudinal axis that runs through the center of the tubular stent. In other words, the individual spindles or loops can independently move up and down, and can spring back to their original position due to the relative stiffness of the wire. The tissue or material that covers the cuff wire has a certain modulus of elasticity such that, when attached to the wire of the cuff, such tissue or material allows the wire spindles to move.

The cuff counteracts the longitudinal ventricular pressure during systole against the prosthesis in the direction of the left ventricle to keep the valve from being displaced or slipping into the ventricle. The tether(s) counteracts this force and is used to maintain the valve position and withstand the ventricular force during ventricular contraction or systole. Accordingly, the entire valve must be positioned in a proper position and cannot be radially misplaced during the deployment process. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction, so the initial deployment must be accurate.

Stent Structure

Preferably, superelastic metal wire, such as Nitinol® wire, is also used for the stent, for the inner wire-based leaflet assembly that is disposed within the stent, and for the cuff wire form. Such stents are available from any number of commercial manufacturers, such as Pulse Systems. Laser cut stents are preferably made from Nickel-Titanium (Nitinol®), but also without limitation made from stainless steel, cobalt chromium, titanium, and other functionally equivalent metals and alloys, or Pulse Systems braided stent that is shape-set by heat treating on a fixture or mandrel.

One key aspect of the stent design is that it be compressible and when released have the stated property that it return to its original (uncompressed) shape. This requirement limits the potential material selections to metals and plastics that have shape memory properties. With regards to metals, Nitinol® has been found to be especially useful since it can be processed to be austenitic, martensitic or super elastic. Martensitic and super elastic alloys can be processed to demonstrate the required compression features.

Laser Cut Stent

One possible construction of the stent envisions the laser cutting of a thin, isodiametric Nitinol® tube. The laser cuts form regular cutouts in the thin Nitinol tube. Secondarily the tube is placed on a mold of the desired shape, heated to the martensitic temperature and quenched. The treatment of the stent in this manner will form a stent or stent/cuff that has shape memory properties and will readily revert to the memory shape at the calibrated temperature.

Leaflet and Inner Wireform

The valve leaflets are held by, or within, a leaflet assembly. In one preferred embodiment of the invention, the leaflet assembly comprises a leaflet wire support structure to which the leaflets are attached and the entire leaflet assembly is housed within the stent body. In this embodiment, the assembly is constructed of wire and stabilized tissue to form a suitable platform for attaching the leaflets. In this aspect, the wire and stabilized tissue allow for the leaflet structure to be compressed when the prosthetic valve is compressed within the deployment catheter, and to spring open into the proper functional shape when the prosthetic valve is opened during deployment. In this embodiment, the leaflet assembly may optionally be attached to and housed within a separate cylindrical liner made of stabilized tissue or material, and the liner is then attached to line the interior of the stent body.

In this embodiment, the leaflet wire support structure is constructed to have a collapsible/expandable geometry. In a preferred embodiment, the structure is a single piece of wire. The wireform is, in one embodiment, constructed from a shape memory alloy such as Nitinol®. The structure may optionally be made of a plurality of wires, including between 2 to 10 wires. Further, the geometry of the wire form is without limitation, and may optionally be a series of parabolic inverted collapsible arches to mimic the saddle-like shape of the native annulus when the leaflets are attached. Alternatively, it may optionally be constructed as collapsible concentric rings, or other similar geometric forms that are able to collapse or compress, then expand back to its functional shape. In certain preferred embodiments, there may be 2, 3 or 4 arches. In another embodiment, closed circular or ellipsoid structure designs are contemplated. In another embodiment, the wire form may be an umbrella-type structure, or other similar unfold-and-lock-open designs. A further preferred embodiment utilizes super elastic Nitinol® wire approximately 0.015" in diameter. In this embodiment, the wire is wound around a shaping fixture in such a manner that 2-3 commissural posts are formed. The fixture containing the wrapped wire is placed in a muffle furnace at a pre-determined temperature to set the shape of the wire form and to impart it's super elastic properties. Secondarily, the loose ends of the wireform are joined with a stainless steel or Nitinol tube and crimped to form a continuous shape. In another preferred embodiment, the commissural posts of the wireform are adjoined at their tips by a circular connecting ring, or halo, whose purpose is to minimize inward deflection of the post(s).

Tether

The tether(s) is attached to the prosthetic heart valve and extend to one or more tissue anchor locations within the heart. In one preferred embodiment, the tether(s) extend downward through the left ventricle, exiting the left ventricle at the apex of the heart to be fastened on the epicardial surface outside of the heart. In another preferred embodiment, the tether is optionally anchored to other tissue locations depending on the particular application of the prosthetic heart valve, such as one or both papillary muscles, septum, and/or ventricular wall.

The tether is made from surgical-grade materials such as biocompatible polymer suture material. Examples of such material include without limitation: ultra high molecular weight polyethylene (UHWPE); 2-0 exPFTE (polytetrafluoroethylene); or 2-0 polypropylene.

DESCRIPTION OF THE FIGURES

Figure 2:
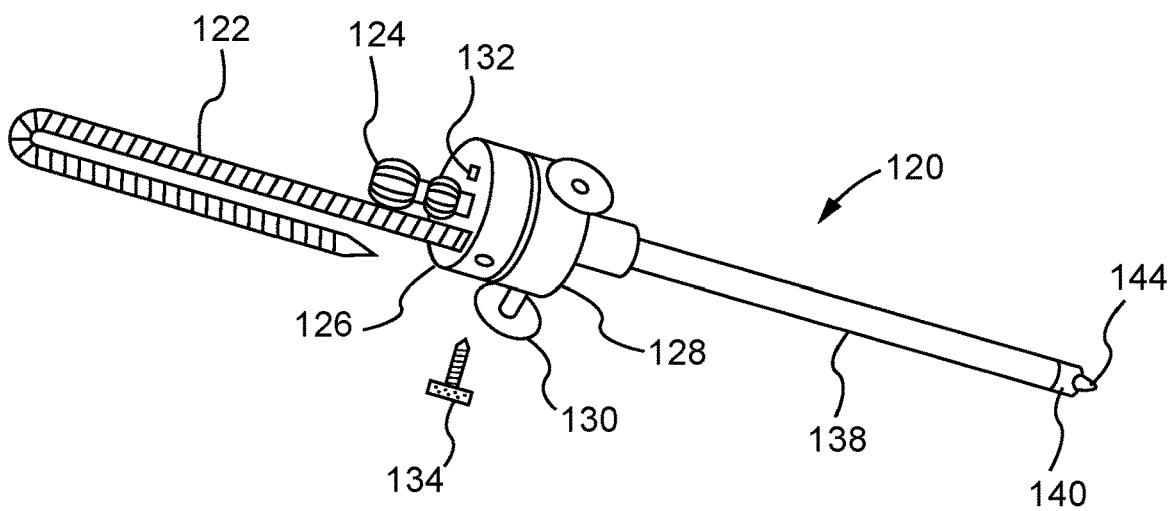
FIG. 2 is a side perspective view of a double-sleeved dilator & catheter assembly with tensioning/traveler strap and two-part retaining collar and gated bore collar.

Referring now to the FIGURES, FIGS. 1 and 2 shows one embodiment of a retrieval and repositioning apparatus. FIG. 1 shows handle 110 and support/pusher rod 116 apparatus for the prosthetic valve retrieval system provided herein. The handle 110 operates with actuator 112 and spring 114 in concert with support rod 116 and tensioning strap 122 to provide a reciprocal motion responsive to the operation of the actuator 112. The support rod 116 is fitted in key slot 132 of retaining collar 126. The traveler strap 122 is loaded into tensioning jaw 118 and upon actuating the handle 112 divides the retaining collar 126 from the gated-bore collar 128. Using tether screw 134 on retaining collar 126 to secure a tether from the valve to be retrieved, the reciprocal motion of the strap 122 and the rod 116 operate to pull the tether. FIG. 2 shows detail of a double-sleeved dilator & catheter assembly 120 for retrieval and repositioning with outer dilator sheath 138 having inner catheter disposed therein. Tapered tip 144 is used to abut strut bundle (not shown) secure the deployed tether. Stylet 124 has a lumen therethrough for accepting the tether and locks into retaingin collar 126. Gated-bore collar 128 has sliding gate 130 for closing off communication with the ventricle to avoid blood loss. Blind distance markers 146 are labelled on the pusher rod to provide the operator with the relative distance that the pusher rod has been advanced. Since the procedure is a catheter-based, non-surgical procedure, the valve is deployed into the patient's heart using only radiographic visualization. Thus, the blind distance markers avoid advancing the pusher rod 116 too far.

Figure 3:
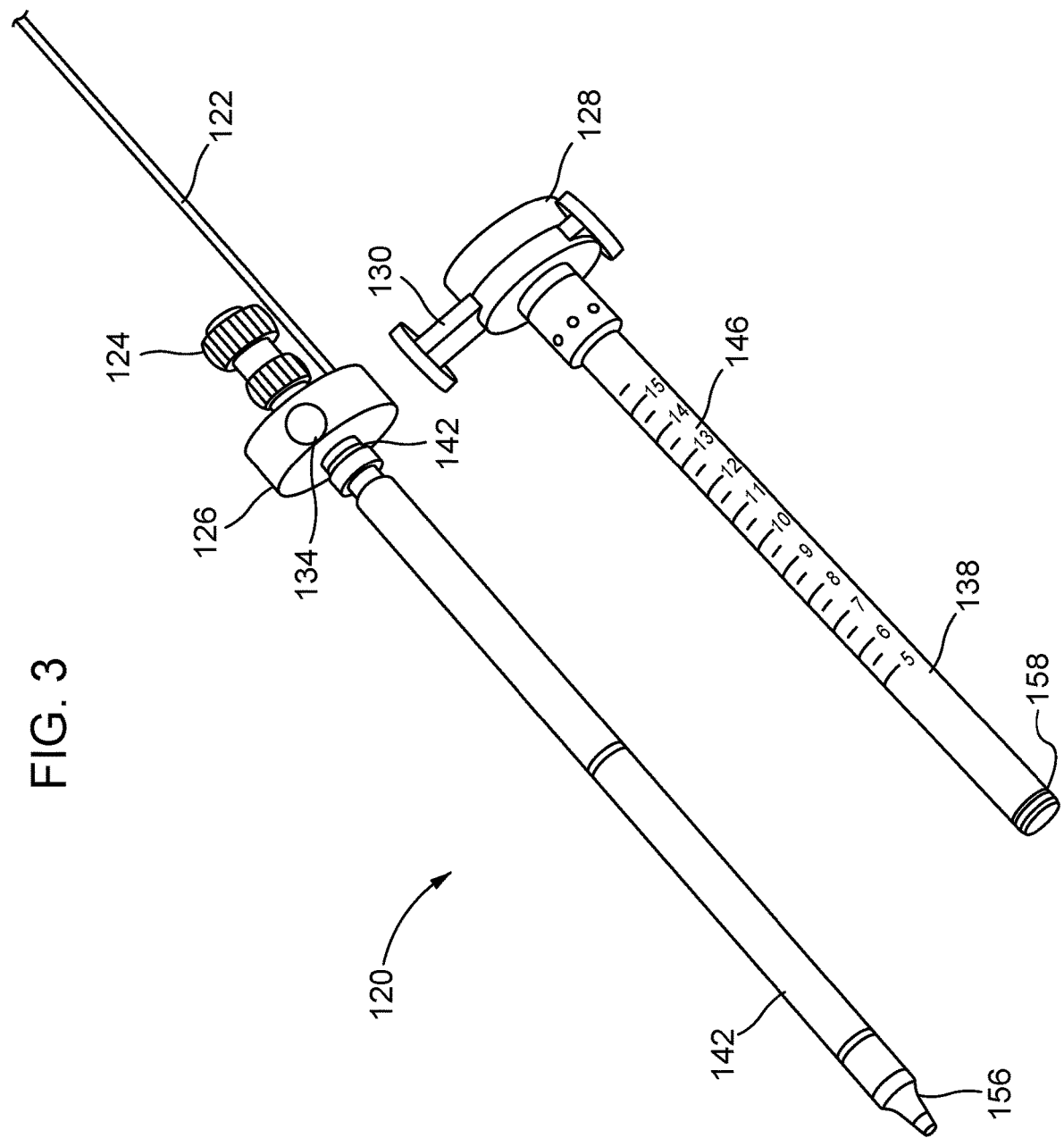
FIG. 3 is a side perspective view of a partially disassembled double-sleeved dilator & catheter assembly with outer sheath having distance/location markings and gated bore collar and the tapered inner catheter disposed within the outer sheath which has tensioning/traveler strap and retaining collar operatively associated therewith.

FIG. 3 shows a partially disassembled double-sleeved dilator & catheter assembly 120 with outer sheath 138 having distance/location markings 146 and gated bore collar 128 and the tapered inner catheter 142 disposed within the outer sheath 138 which has tensioning/traveler strap 122 and retaining collar 126 operatively associated therewith. FIG. 3 also shows removable stylet 124, tether screw 134 and gasket 142 on retaining collar/inner catheter base 126. FIG. 3 shows tapered tip 156 at the distal end of inner catheter 140. FIG. 3 shows sliding gate 130 on the gated-bore collar/dilator base 128 and radio band 158 at the distal end of dilator sheath 138.

Figure 4:
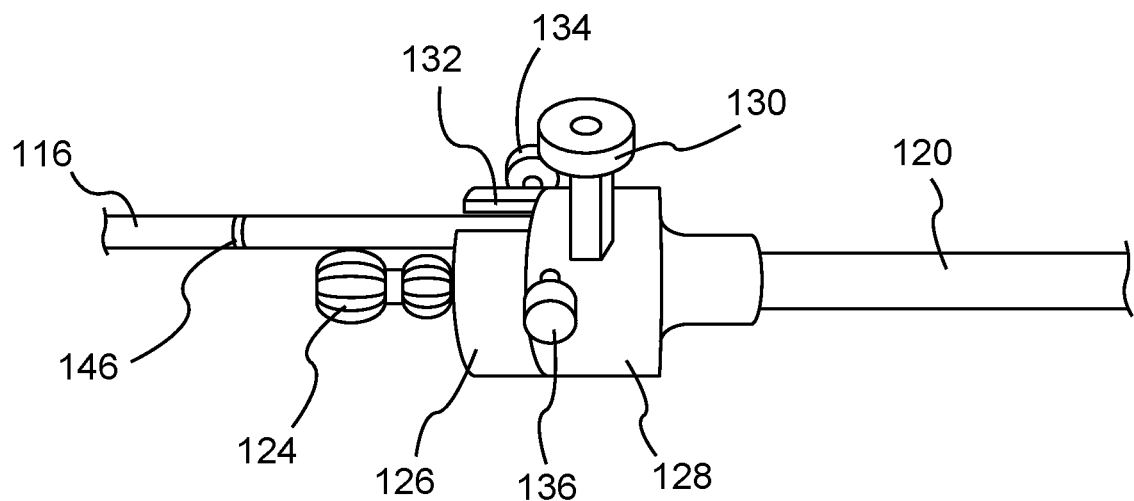
FIG. 4 is a side detailed view of two-part retaining collar and gated bore collar showing how support rod fits into the key slot of the retaining collar and the double-sleeved retrieval and repositioning catheter extends from gated bore collar.

FIG. 4 shows a two-part retaining collar 126 and gated bore collar 128 showing how support rod 116 fits into the key slot 132 of the retaining collar 126 and the double-sleeved retrieval and repositioning catheter 120 extends from gated bore collar 128. FIG. 4 also shows tether screw 134 on retaining collar for securing the captured tether, as well as rod screw 136 located on the gated-bore collar 128 for securing the position of the rod 116 within the gated-bore collar 128. Stylet 124, distance marker 146 and sliding gate 130 are also shown.

Figure 5:
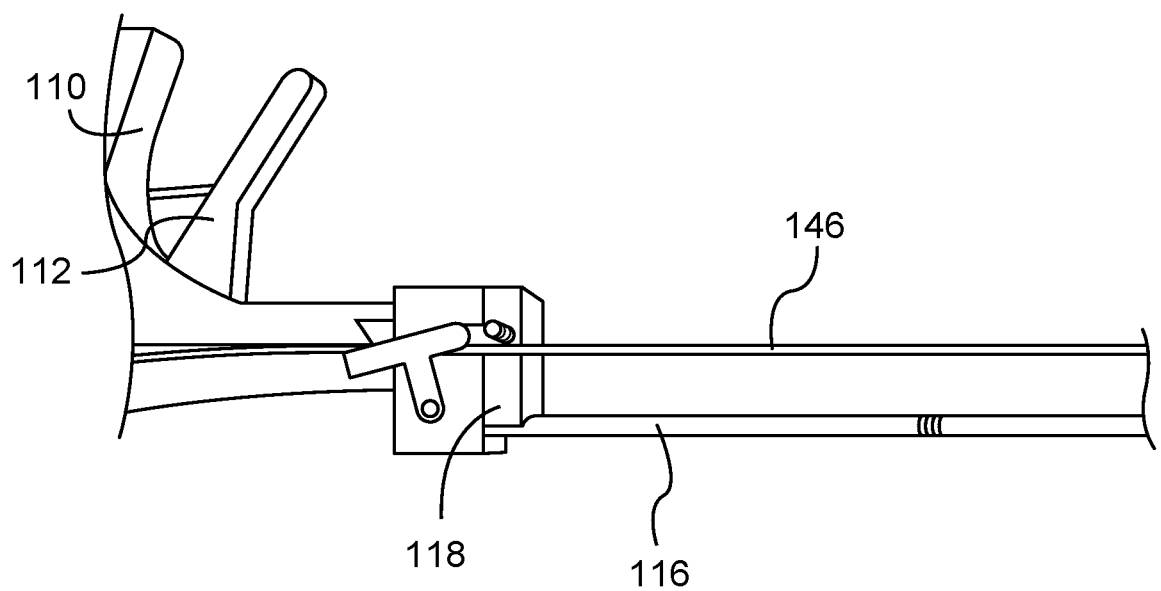
FIG. 5 is a side detailed view of the handle and actuator with support/pusher rod and traveler strap disposed within the strap tensioning jaw.

FIG. 5 shows the handle 110 and actuator 112 with support/pusher rod 116 and traveler strap 122 disposed within the strap tensioning jaw 118. Operating the actuator 112 pulls the strap 122 into the tensioning jaw 118 towards the handle 110.

Figure 6:
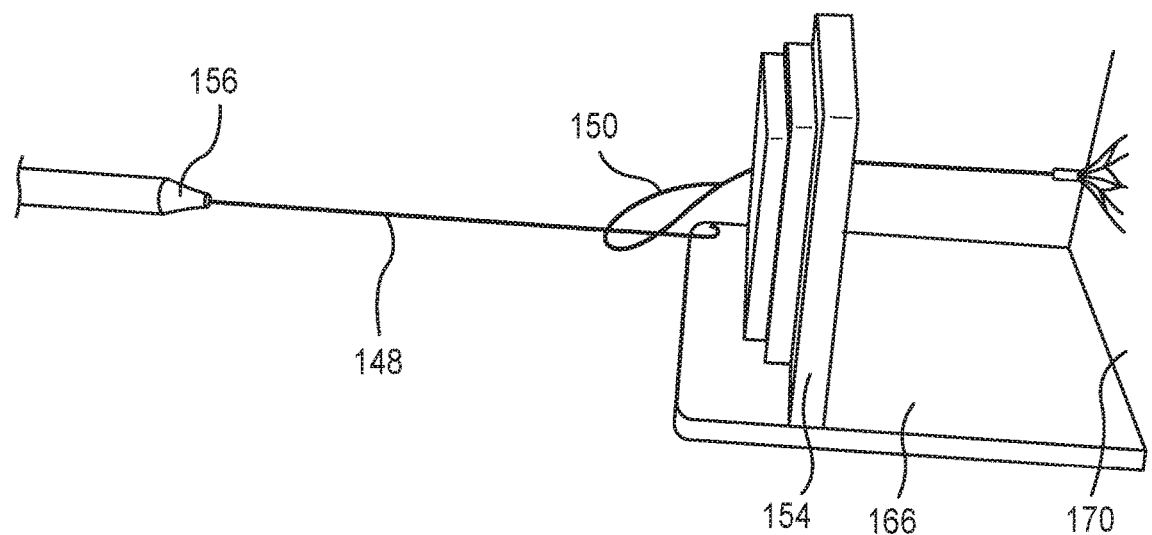
FIG. 6 is a side perspective view of the tapered conical catheter tip having capture wire extending therethrough and capturing the tether of a deployed prosthetic valve in a demonstration model of a body cavity such as a ventricle.

FIG. 6 shows an over-the-wire catheter-based equipment delivery technique and specifically shows the tapered conical catheter tip 156 having capture wire 148 extending therethrough and capturing the tether 150 of a deployed prosthetic valve in a demonstration model 166 of a body cavity such as a ventricle. Demonstration model includes simulated body wall access port 154 anatomically spaced from simulated annulus 170 and shows in cross-section how the retrieval device works in the context of a body cavity.

Figure 7:
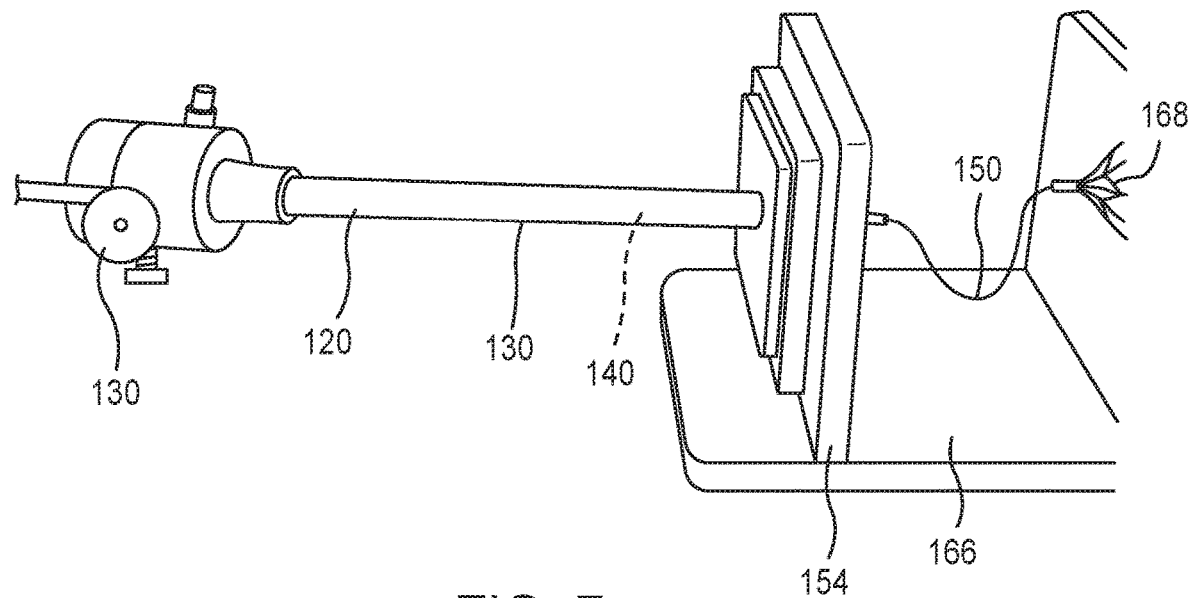
FIG. 7 is a side perspective view of the double-sleeved retrieval and repositioning catheter that has been partially advanced into the ventricle or cavity of the demonstration model of a ventricle towards the valve/device to be retrieved while the tether slack is reeled in or gathered.

FIG. 7 shows the double-sleeved retrieval and repositioning catheter 120 that has been partially advanced through the body wall access port 154 and into the ventricle or cavity of the demonstration model 166 of a ventricle towards the valve/device 168 to be retrieved while the tether 150 slack is reeled in or gathered. The dilator outer sheath 138 of catheter 120 establishes a conduit for delivery of the retrieval and repositioning inner catheter 140 (not shown). Sliding gate 130 prevents blood loss down the catheter assembly during cavity access.

Figure 8:
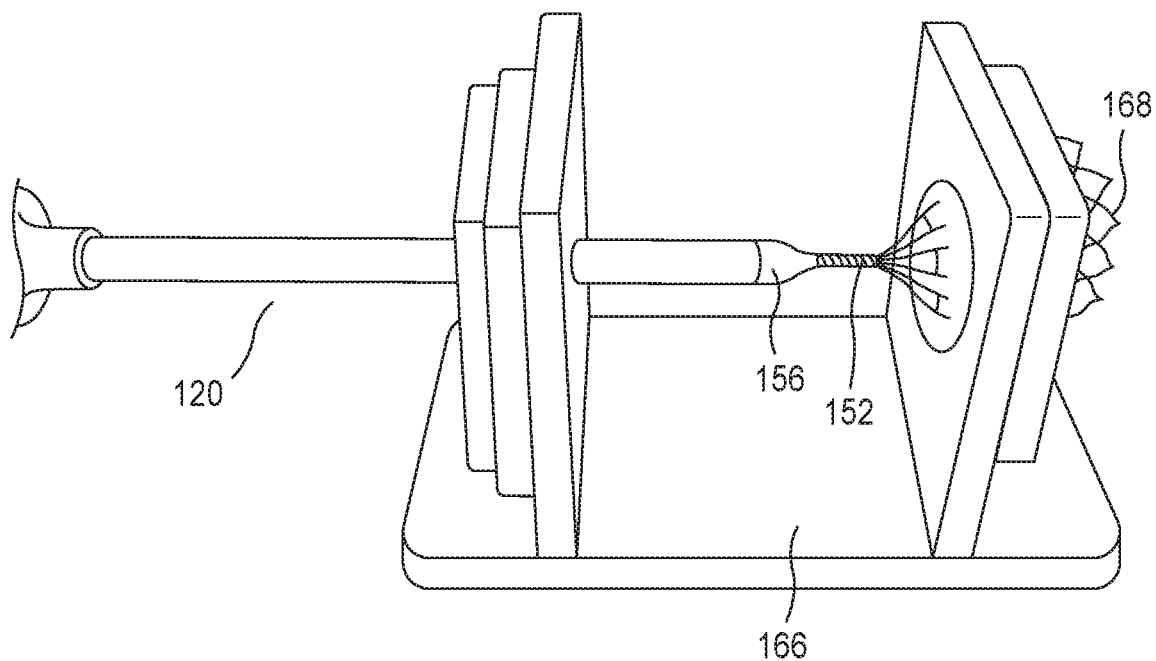
FIG. 8 is a side perspective view of the double-sleeved retrieval and repositioning catheter that has been advanced into the ventricle or cavity of a demonstration model of a ventricle towards the valve/device to be retrieved while the tether slack is reeled in or gathered.
Figure 9:
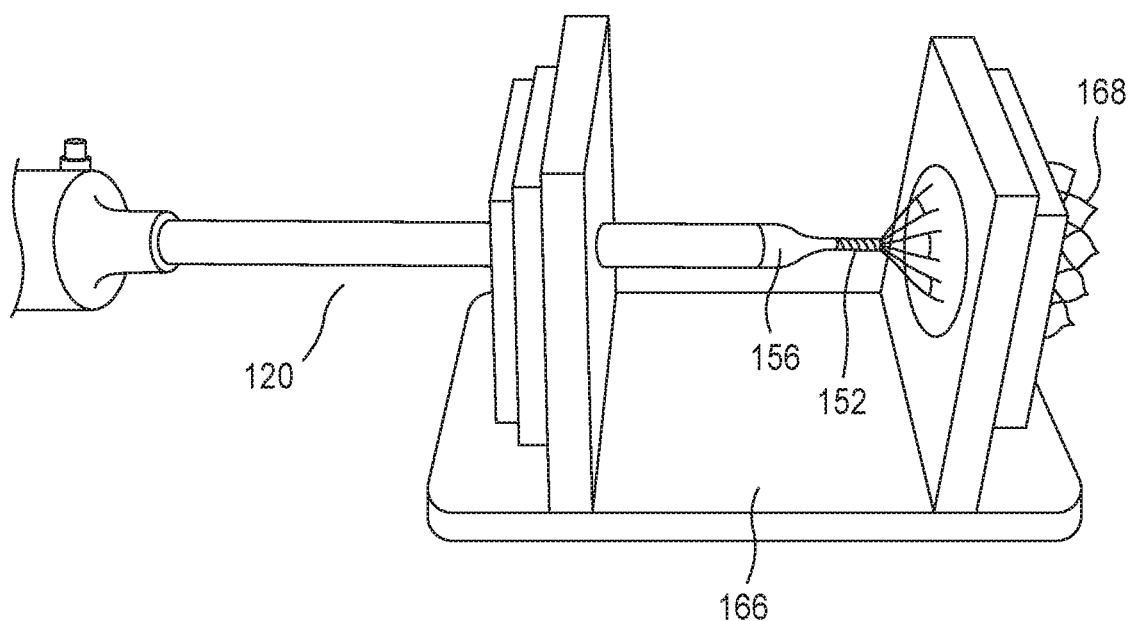
FIG. 9 is a side perspective view of the double-sleeved retrieval and repositioning catheter that has been advanced into the ventricle or cavity of the demonstration model of a ventricle towards the valve/device to be retrieved while the tether slack is reeled in or gathered and the tapered tip engages the strut bundle of the valve.

FIGS. 8 and 9 show the double-sleeved retrieval and repositioning catheter 120 that has been advanced into the ventricle or cavity of a demonstration model 166 of a ventricle towards the valve/device 168 to be retrieved while the tether 150 slack is reeled in or gathered. FIG. 8 specifically shows how tapered tip 156 is advanced until it abuts the strut bundle 152. The positioning is used to control the release of the deployed valve 168 from the annulus 170.

Figure 10:
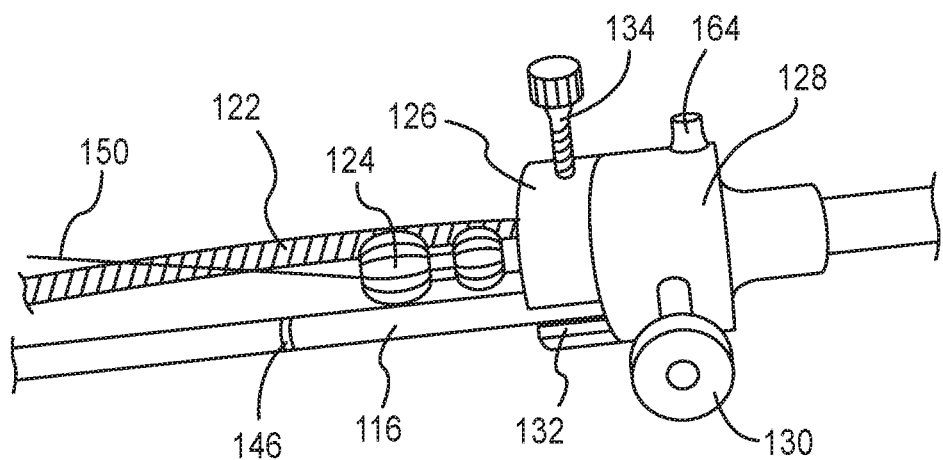
FIG. 10 is a perspective view of the retaining collar and gated-bore collar with the captured tether exiting the proximal end of the stylet and tether screw in an open position prior to adjustment to secure the tether.

FIG. 10 shows the retaining collar 126 and gated-bore collar 128 with the captured tether 150 exiting the proximal end of the stylet 124 and tether screw 134 in an open position prior to adjustment to secure the tether 150. FIG. 10 also shows rod 116 disposed with key slot/guide rod aperture 132 and traveler strap 122 extending parallel to the rod towards the handle 110 (not shown). Distance marker 146 is shown on rod 116. Sliding gate 130 is also shown on dilator base/gated-bore collar 128. Collar luer 164 is shown and provides a port for adding saline and/or removing blood or fluids.

Figure 11:
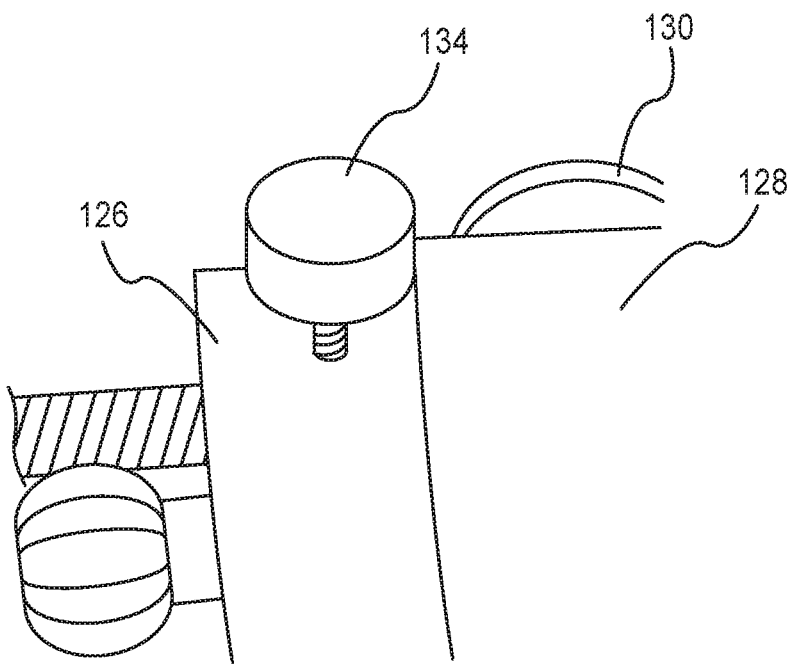
FIG. 11 is a perspective view of the retaining collar and gated-bore collar with the tether screw fully adjusted into a locked or closed position for securing the tether.

FIG. 11 shows the retaining collar 126 and gated-bore collar 128 with the tether screw 134 fully adjusted into a locked or closed position for securing the tether 150. Sliding gate 130 is also shown on dilator base/gated-bore collar 128.

Figure 12:
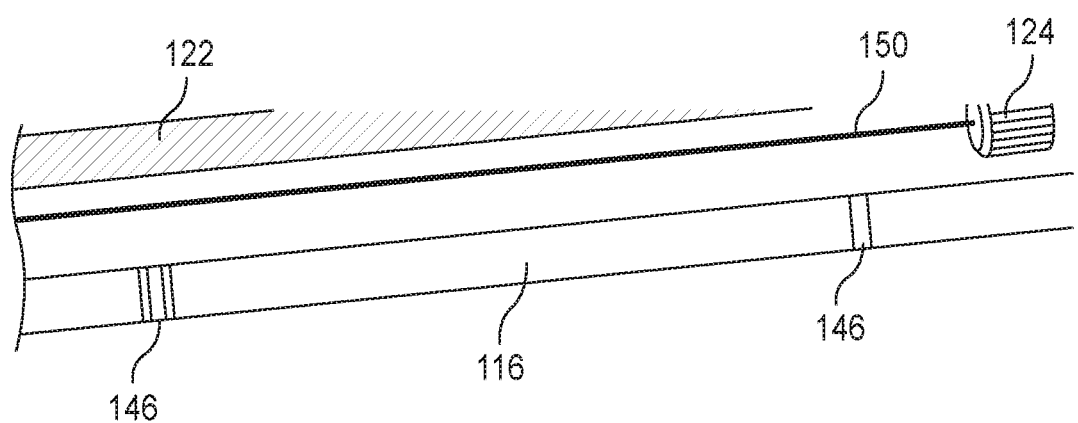
FIG. 12 is a perspective view of the support rod/pusher rod after the tether has been secured and shows distance markers.

FIG. 12 shows the support rod/pusher rod 116 after the tether 150 exiting stylet 124 has been secured and shows distance markers 146. Tensioning strap/traveler strap 122 is shown parallel to rod 116.

Figure 13:
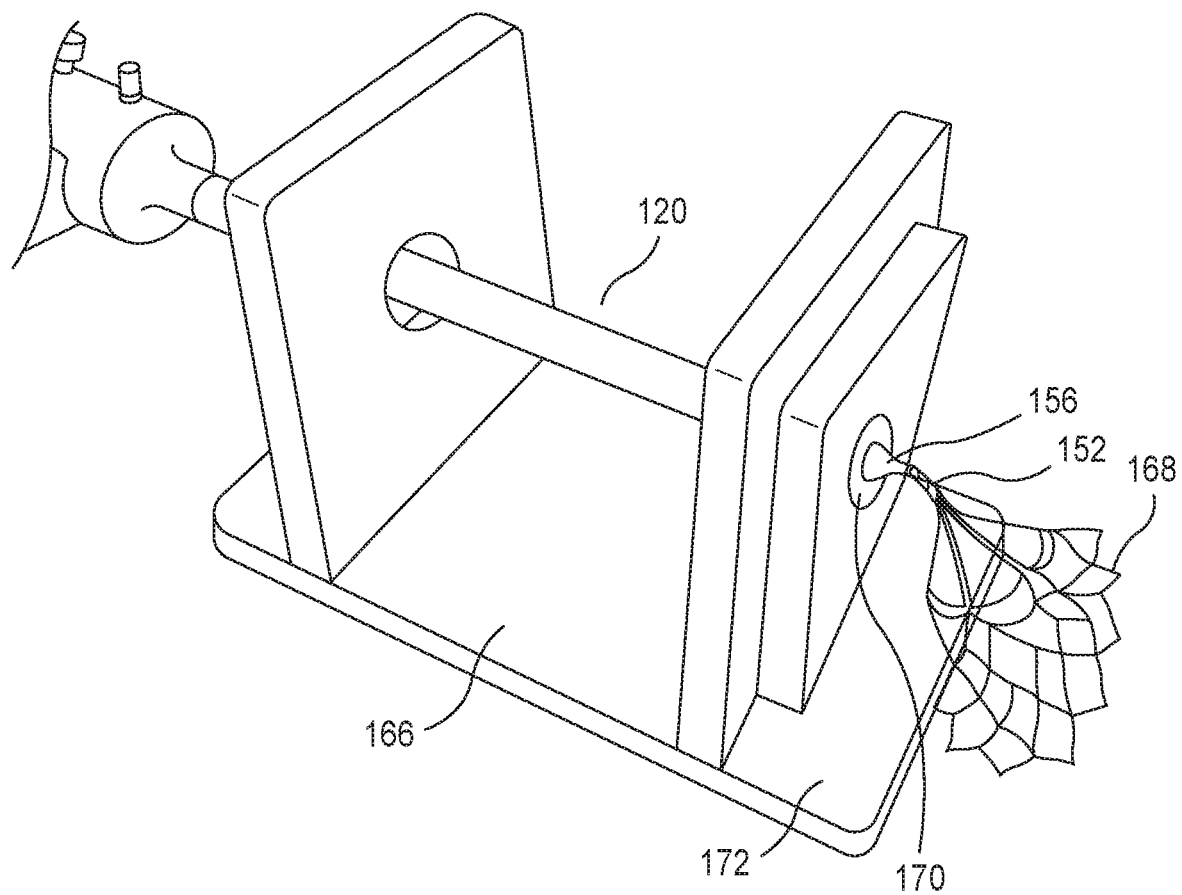
FIG. 13 is a perspective view of the double-sleeved catheter that has been advanced through the ventricle or cavity of the demonstration model of a ventricle beyond the location of the valve annulus of the demonstration model.

FIG. 13 shows the double-sleeved catheter 120 that has been advanced through the ventricle or cavity of the demonstration model 166 of a ventricle beyond the location of the valve annulus of the demonstration model. FIG. 13 shows the tapered tip 156 of the inner catheter 140 engaging the strut bundle 152 of the valve and expelling the deployed valve 168 from the annulus 170 into an atrial location 172 of the demonstration model 166.

Figure 14:
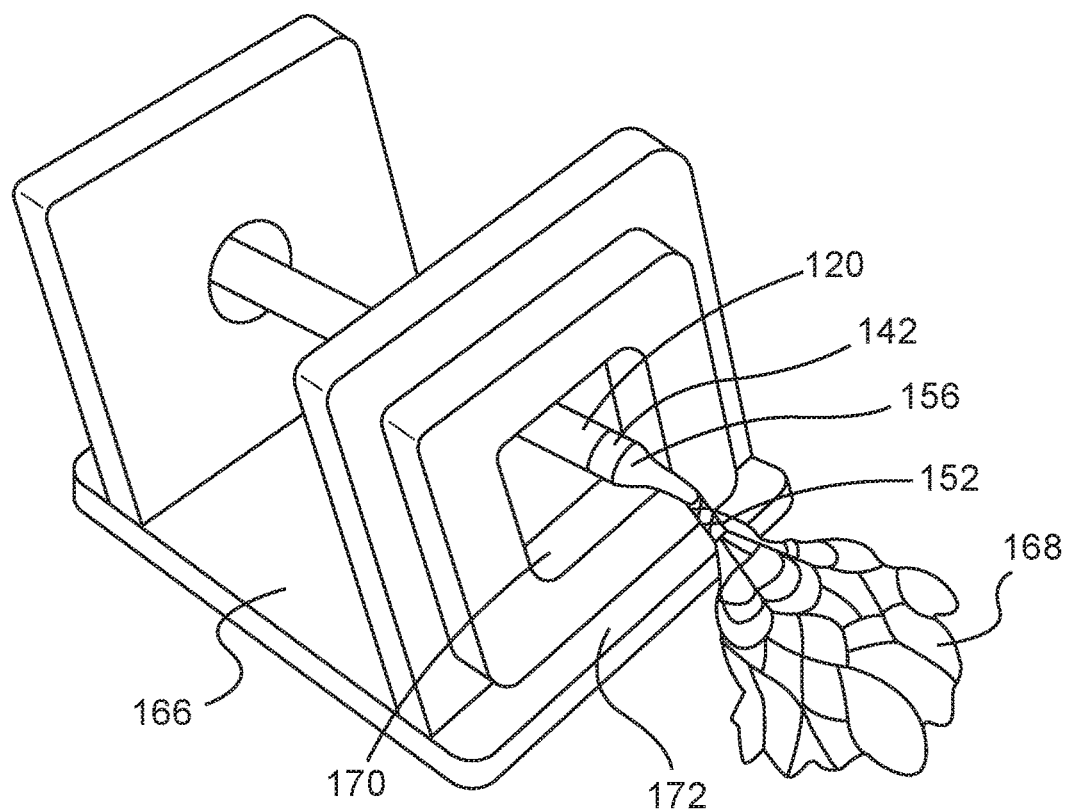
FIG. 14 is a perspective detail view of the double-sleeved retrieval and repositioning catheter that has been advanced through the ventricle or cavity of the demonstration model of a ventricle beyond the location of the valve annulus of the demonstration model.

FIG. 14 shows the double-sleeved retrieval and repositioning catheter 120 that has been advanced through the annulus 170 of the ventricle or cavity of the demonstration model 166 of a ventricle beyond the location of the valve annulus 170 of the demonstration model. FIG. 14 shows the tapered tip 156 of the inner catheter 142 engaging the strut bundle 152 of the valve 168 and expelling the deployed valve 168 from the annulus 170 into an atrial space 172 of the demonstration model 166.

Figure 15:
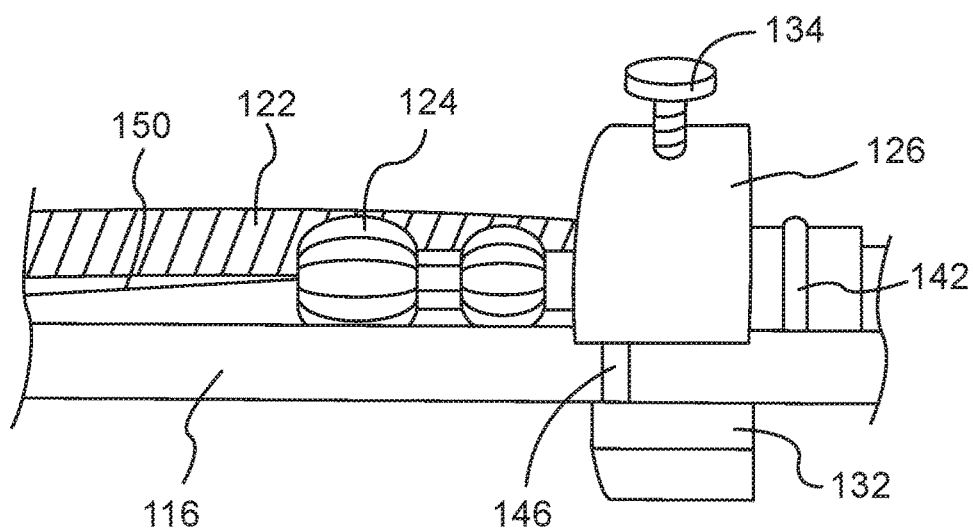
FIG. 15 is a detail view of the retaining collar with the tether screw fully adjusted into a locked or closed position for securing the tether and the marker on the support rod illustrating the initial pre-retrieval distance that actuating the traveler strap has accomplished during the initial capture and securing of the valve to be retrieved.

FIG. 15 shows the retaining collar 126 with the tether screw 134 fully adjusted into a locked or closed position for securing the tether 150, seen exiting the stylet 124. Marker 146 on the support rod 116 illustrates the initial pre-retrieval distance that actuating the traveler strap 122 has accomplished during the initial capture and securing of the valve to be retrieved. Gasket 142 and key slot/rod aperture 132 are shown on inner catheter base 126.

Figure 16:
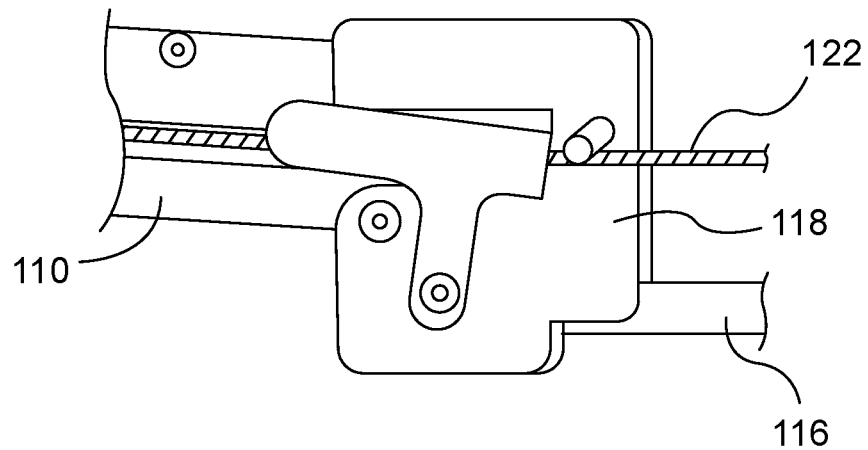
FIG. 16 is a detail view of the traveler strap entering the tensioning jaw.

FIG. 16 shows the traveler strap 122 entering the tensioning jaw 118. Support rod 116 and handle 110 are shown mounted with tensioning jaw 118.

Figure 17:
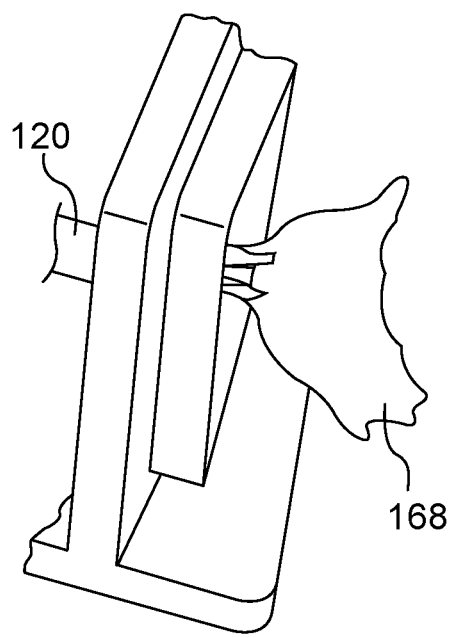
FIG. 17 is a detail view of the misaligned valve prior to being re-positioned into a better alignment, e.g. A2 conforming segment of the atrial cuff on the valve aligned with A2 location of native annulus.

FIG. 17 shows the misaligned valve 168 prior to being re-positioned into a better alignment under control of the dilator assembly 120, e.g. A2 conforming segment of the atrial cuff on the valve aligned with A2 location of native annulus.

Figure 18:
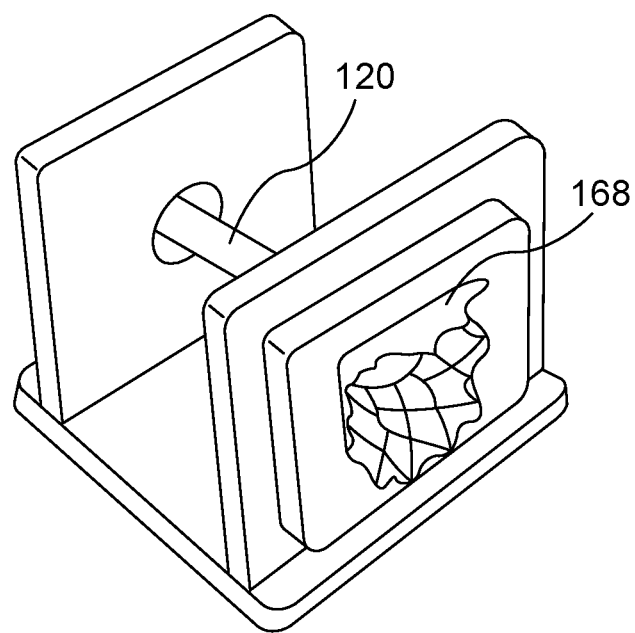
FIG. 18 is a detail view of the valve after re-positioning and redeployment into the valve annulus of the demonstration model framework.

FIG. 18 shows the valve 168 after re-positioning and redeployment into the valve annulus of the demonstration model framework 166 while under control of the dilator assembly 120.

Figure 19:
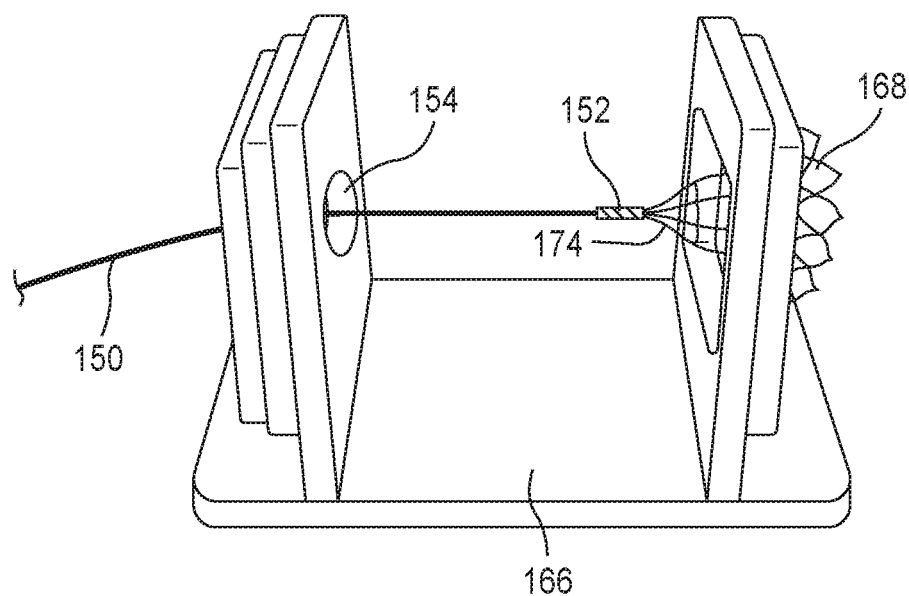
FIG. 19 is a side view of the retrieved and re-positioned valve mounted in the tethered valve deployment demonstration model, e.g. left ventricle, right ventricle, body cavity, etc. and shows the struts, strut bundle, and tether extending across the cavity and out through the body wall access port.

FIG. 19 shows the retrieved and re-positioned valve 168 mounted in the tethered valve deployment demonstration model 166, e.g. left ventricle, right ventricle, body cavity, etc. and shows the struts 174, strut bundle 152, and tether 150 extending across the cavity and out through the body wall access port 154.

Figure 20:
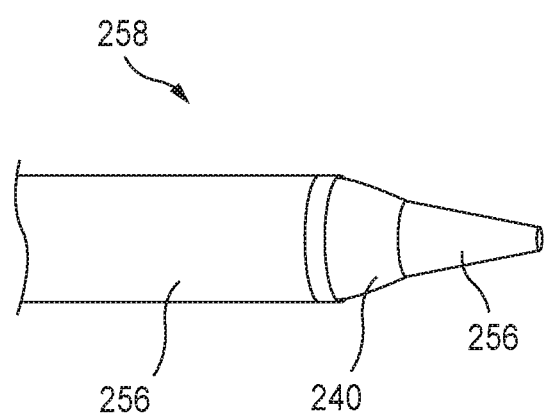
FIG. 20 is a side view of a three-part triple-sheathed retrieval and removal catheter having a flared outer dilator sheath with an intermediate beveled catheter disposed within and an inner catheter having a tapered tip disposed within the intermediate beveled catheter.

FIG. 20 shows a three-part triple-sheathed retrieval and removal catheter 258 having a flared outer dilator sheath 260 with an intermediate beveled catheter 240 disposed within and an inner catheter 242 having a tapered tip 256, said inner catheter 242 disposed within the intermediate beveled catheter 240. For removal, in operation the three-part catheter assembly uses the tapered tip 256 to engage and control the valve or device to be removed. The inner catheter 242 is then slightly withdrawn to allow the intermediate beveled catheter 240 to engage the struts 174 of the valve. Then, the intermediate beveled catheter 240 is slightly withdrawn to allow the outer-most flared dilator sheath 260 to compress and extract the valve. This multi-staged process allows the expandable valves, which have a large expansion force, to be compressed and withdrawn into a catheter. Without addressing such issues, such as is provided by these stages, there is an increased chance that the valve struts will break, the valve will be damaged, or the valve will get stuck and not be compressed, making catheter-based retrieval difficult and potentially unfeasible.

Figure 21:
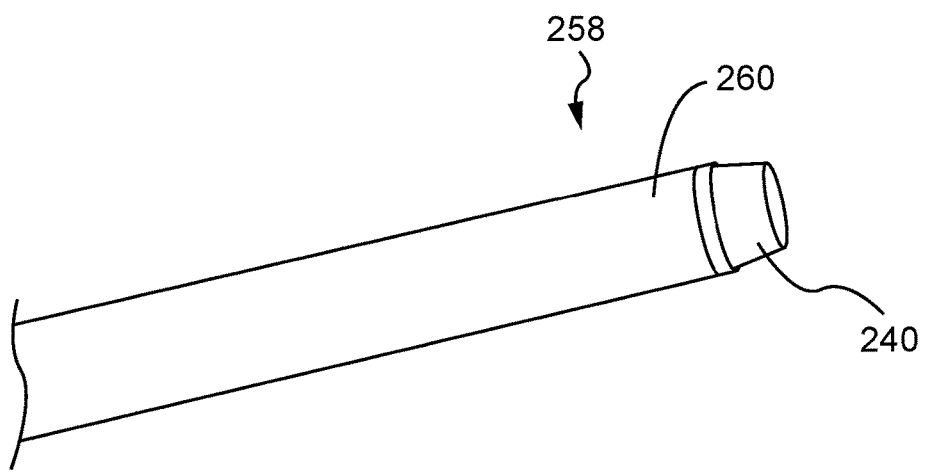
FIG. 21 is a detail view of the two outermost catheters of the triple-sheathed retrieval and removal catheter and shows a flared outer dilator sheath with an intermediate beveled catheter disposed within.

FIG. 21 shows the two outermost catheters of the triple-sheathed retrieval and removal catheter 258 and shows a flared outer dilator sheath 260 with an intermediate beveled catheter 240 disposed within.

Figure 22:
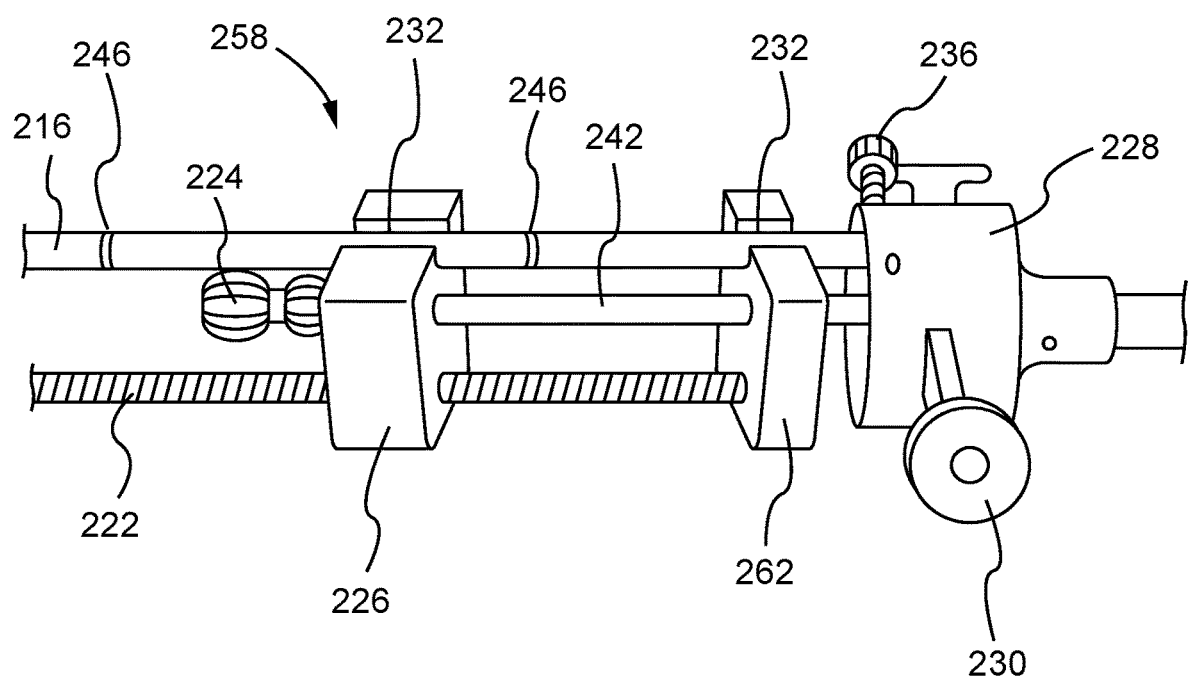
FIG. 22 is a detail view of the assembled retrieval and removal catheter apparatus and shows support rod extending from the retaining collar across a collar stabilizer to the gated bore collar, traveler strap attached to the retaining collar and sliding gate mounted on the gated-bore collar, with the triple-sheathed catheter attached to a distal end of the gated-bore collar and stylet and inner catheter extending through the axis of the entire apparatus.

FIG. 22 shows the assembled retrieval and removal catheter apparatus 258 and shows support rod 216 extending from the retaining collar 226 across a secondary collar 262 to the gated bore collar 228, traveler strap 222 attached to the retaining collar 226 and sliding gate 230 mounted on the gated-bore collar 228, with the triple-sheathed catheter 258 attached to a distal end of the gated-bore collar 228 and stylet 224 and inner catheter 242 extending through the axis of the entire apparatus. Key slot/Rod aperture 232 and distance markers 246 are shown along with rod screw 236. In operation, the use of multiple stages requires the use of multiple catheter bases, with each engaging the support rod 216 and the retaining collar/inner catheter base 226 and secondary collar/intermediate base 262 operationally attached to the traveler strap for advancing the tethered valve in staged steps.

Figure 23:
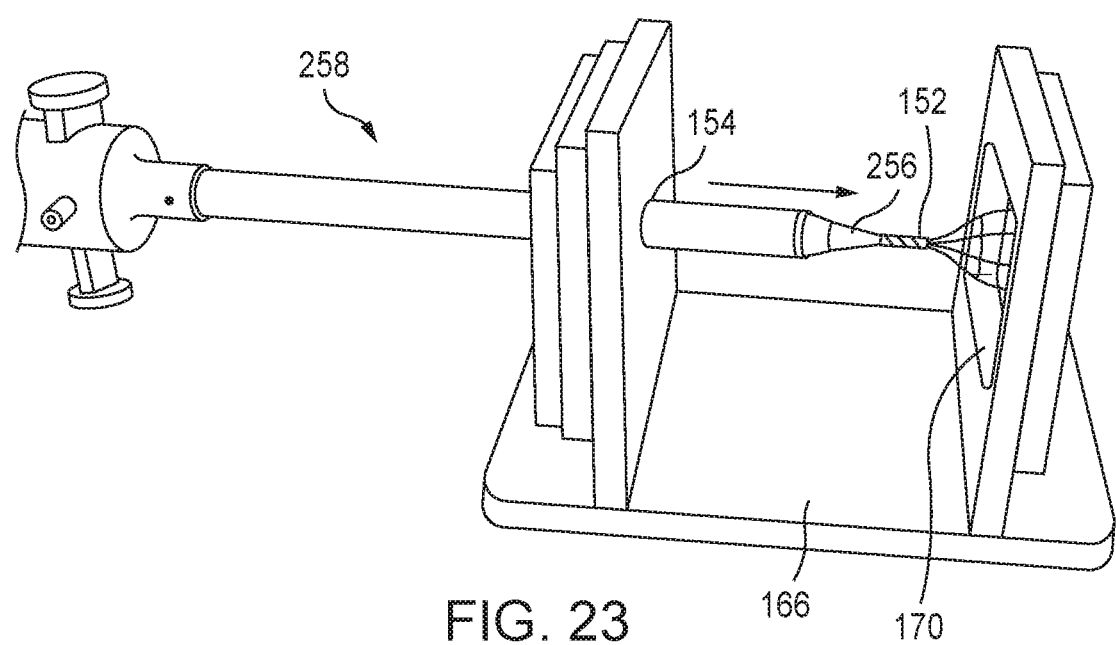
FIG. 23 is a perspective view of the triple-sheathed catheter that has been advanced through the ventricle or cavity of the demonstration model of a ventricle beyond the location of the valve annulus of the demonstration model.

FIG. 23 shows the triple-sheathed catheter 258 that has been advanced through the body wall access port 154 of the the ventricle or cavity of the demonstration model 166. Once the valve or device is under control, the valve or device is expelled from the annulus 170. FIG. 23 shows the tapered tip 256 of the inner catheter engaging the strut bundle 152 of the valve just prior to expelling the deployed valve from the annulus 170 into an atrial location of the demonstration model.

Figure 24:
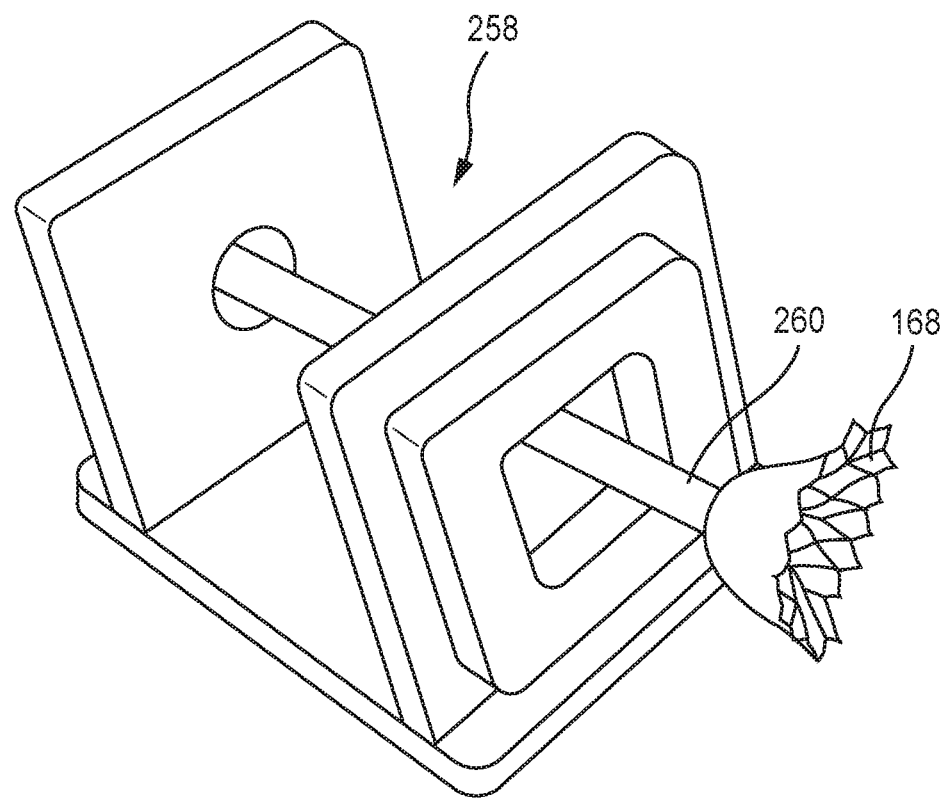
FIG. 24 is a perspective view of the triple-sheathed removal catheter and shows the valve partially withdrawn in the flared outer dilator sheath after the inner catheter has taken control of the strut bundle using the tapered tip and the intermediate beveled catheter has controllably collapsed and compressed the valve struts.

FIG. 24 shows the triple-sheathed removal catheter 258 and shows the valve 168 partially withdrawn in the flared outer dilator sheath 260 after the inner catheter 242 (not seen) has taken control of the strut bundle 152 (not seen) using the tapered tip 256 and the intermediate beveled catheter 240 (not seen) has controllably collapsed and compressed the valve struts 174 (not seen).

Figure 25:
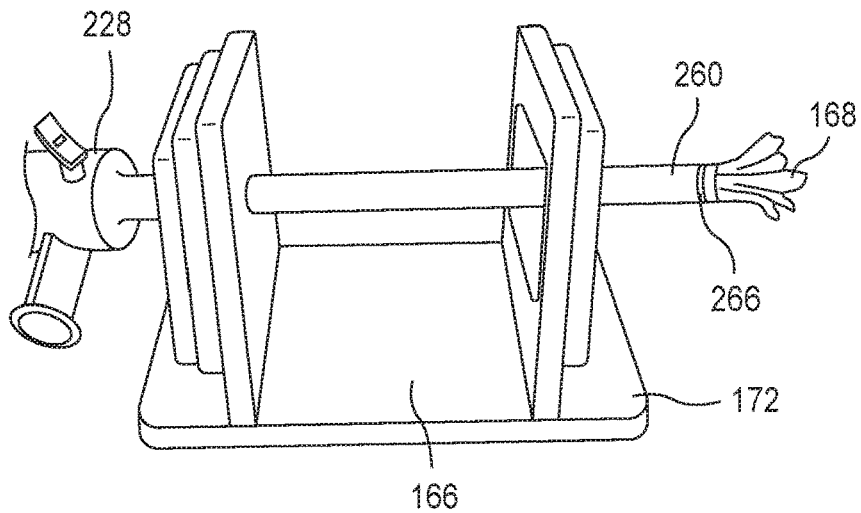
FIG. 25 is a side perspective view of the valve being further drawn into the protective flared end of the flared outer dilator sheath.

FIG. 25 shows the valve 168 being further drawn into the protective flared end of the flared outer dilator sheath 260. FIG. 25 also shows the outer dilator sheath catheter 260 extending across the lumen of the ventricle of the model with the gated-bore collar 228 outside of the body wall access port 154 (proximal side) and the valve being removed from inside an atrial space 172 of the demonstration model 166.

Figure 26:
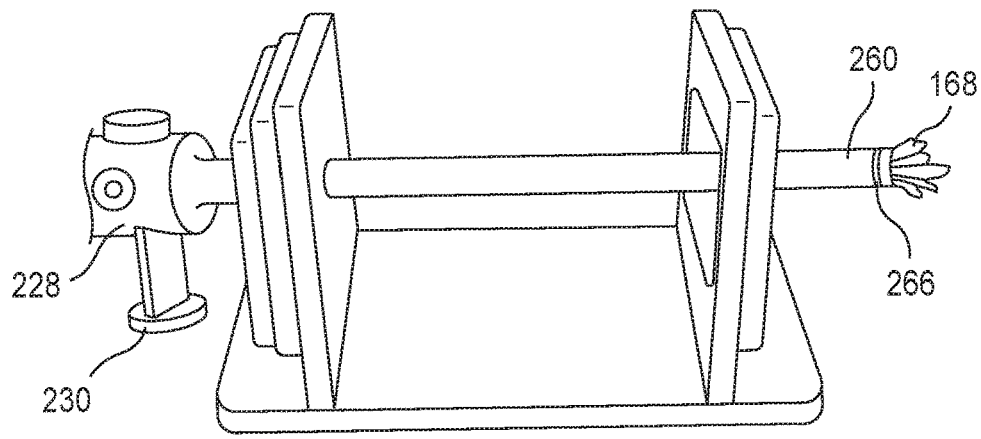
FIG. 26 is a side perspective view of the valve being further drawn into the protective flared end of the flared outer dilator sheath.

FIG. 26 shows the valve 168 being further drawn into the protective flared end of the flared outer dilator sheath 260. FIG. 26 also shows radio-marker band 266 at the tip of the outer catheter/dilator sheath 260. Sliding gate 230 of dilator base/gated collar 228 is shown 'outside' of the cavity and sliding gate 230 is in the open (lumen) position which is used during valve removal.

Figure 27:
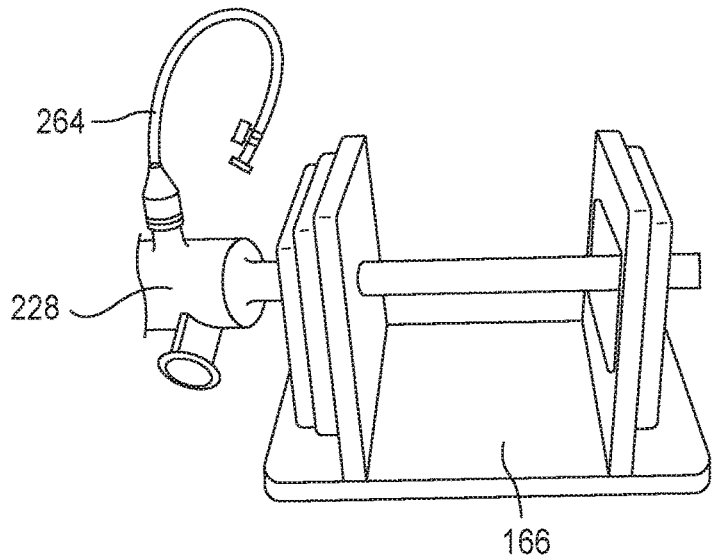
FIG. 27 is a side perspective view and shows the valve entirely removed and withdrawn into the outer catheter.

FIG. 27 shows the valve entirely removed and withdrawn into the outer catheter and out of the simulated body cavity 166. FIG. 27 shows luer 264 on the outer collar 228.

For convenience, the following parts list is provided corresponding to the drawing figures herein to assist in better understanding the inventive subject matter.

RETRIEVAL PARTS 110 handle
112 actuator
114 spring
116 support rod
118 (strap) tensioning jaw
120 double-sheathed dilator assembly
122 (tensioning) strap
124 stylet
126 retaining collar/inner catheter base
128 gated bore collar/dilator base
130 sliding gate
132 key slot/guide rod aperture
134 tether screw
136 rod screw
138 dilator (outer) sheath
140 inner catheter
142 gasket
144 strut coupler
146 rod distance markers
148 capture wire
150 tether
152 strut bundle
154 body wall access port
156 tapered tip
158 radio band
162 collar stabilizer
164 collar luer 166 demonstration model
168 valve
170 annulus
172 atrial space
174 struts
210 handle
212 actuator
214 spring
216 support rod
218 (strap) tensioning jaw
222 (tensioning) strap
224 stylet
226 retaining collar
228 gated bore collar
230 sliding gate
232 key slot/rod aperture
234 tether screw
236 rod screw
240 intermediate beveled catheter
242 inner catheter
244 strut coupler
246 rod distance markers
248 capture wire
256 tapered tip
258 triple-sheathed dilator assembly
260 flared dilator (outer) sheath
262 secondary collar
264 collar luer
266 radio band The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A method for capturing a tethered prosthetic heart valve implanted within a heart of a patient to retrieve and re-position the prosthetic heart valve, the method comprising:
   inserting a retrieval and repositioning device at least partially into a heart of patient in which a tethered and expandable prosthetic heart valve is implanted;
   capturing and retracting a tether coupled to the expandable prosthetic heart valve into a lumen of a catheter of the retrieval and repositioning device; and
   repositioning the expandable prosthetic heart valve within the heart of the patient using the retrieval and repositioning device,
   wherein the tethered and expandable prosthetic heart valve includes the tether fixedly coupled to the expandable prosthetic heart valve such that after implantation of the expandable prosthetic heart valve, the tether is anchored to tissue of the heart.

2. The method of claim 1, further comprising:
   after the capturing and retracting the tether, securing the tether to a portion of the retrieval and removal device with a locking device.

3. The method of claim 1, further comprising:
   prior to repositioning the expandable prosthetic heart valve, actuating an actuator of the retrieval and repositioning device such that the prosthetic heart valve is pulled proximally and a portion of the prosthetic heart valve is at least partially engaged with the retrieval and repositioning device.

4. The method of claim 3, wherein the repositioning the expandable prosthetic heart valve within the heart of the patient includes actuating the actuator of the retrieval and repositioning device such that the prosthetic heart valve is moved distally within the heart and released from engagement with the retrieval and repositioning device.

5. The method of claim 1, wherein:
   the capturing and retracting the tether includes actuating an actuator of the retrieval and repositioning device such that an inner catheter of the retrieval and repositioning device is moved distally and a distal tip of the inner catheter engages the prosthetic heart valve within the heart.

6. The method of claim 1, wherein the inserting the retrieval and repositioning device includes inserting the retrieval and repositioning device by directly accessing the heart through the intercostal space, or using an apical approach to enter a heart ventricle.

7. The method of claim 1, wherein the inserting the retrieval and repositioning device includes inserting the retrieval and repositioning device by directly accessing the heart through a thoracotomy, sternotomy, or a minimally-invasive thoracic, thoracoscopic, or transdiaphragmatic approach to enter the left ventricle.

8. A method of capturing a tethered expandable prosthetic heart valve implanted within a heart to retrieve and remove the prosthetic heart valve from the heart, the method comprising:
   inserting a retrieval and removal device into a heart of a patient containing a tethered and expandable prosthetic heart valve wherein the tethered and expandable prosthetic heart valve includes the tether fixedly coupled to the expandable prosthetic heart valve and the tether is anchored to tissue of the heart;
   capturing and retracting the tether attached to the expandable prosthetic heart valve into a first lumen of the retrieval and removal device;
   capturing the expandable prosthetic heart valve within a second lumen of the retrieval and removal device; and
   removing the retrieval and removal device with the captured prosthetic heart valve from the body cavity of the patient within.

9. The method of claim 8, further comprising:
   prior to the removing the retrieval and removal device with the captured prosthetic heart valve, withdrawing the captured prosthetic heart valve within a third lumen of the retrieval and removal device.

10. The method of claim 8, wherein:
    the capturing the expandable prosthetic heart valve within a second lumen of the retrieval and removal device includes actuating an actuator of the retrieval and removal device such that an inner catheter of the retrieval and removal device is pulled proximally within a lumen of an intermediate catheter of the retrieval and removal device and at least a portion of the prosthetic heart valve is pulled proximally within the lumen of the intermediate catheter of the retrieval and removal device.

11. The method of claim 8, wherein:
    the capturing and retracting the tether includes actuating an actuator of the retrieval and removal device such that an inner catheter of the retrieval and removal device is moved distally and a distal tip of the inner catheter engages the prosthetic heart valve within the heart.

12. The method of claim 8, wherein the inserting the retrieval and repositioning device includes inserting the retrieval and repositioning device by directly accessing the heart through the intercostal space, or using an apical approach to enter a heart ventricle.

13. The method of claim 8, wherein the inserting the retrieval and repositioning device includes inserting the retrieval and repositioning device by directly accessing the heart through a thoracotomy, sternotomy, or a minimally-invasive thoracic, thorascopic, or transdiaphragmatic approach to enter the left ventricle.

14. The method of claim 8, further comprising:
after the capturing and retracting the tether, securing the tether to a portion of the retrieval and removal device with a locking device.

* * * * *